United States Patent [19]

Grassmann et al.

[11] 4,349,740
[45] Sep. 14, 1982

[54] APPARATUS FOR DISPLAYING FLUOROSCOPIC TOMOGRAPHIC IMAGES OF THE BODY

[75] Inventors: Peter Grassmann; Kurt Dietz; Friedrich Meinel, all of Erlangen, Fed. Rep. of Germany

[73] Assignee: Siemens Aktiengesellschaft, Berlin & Munich, Fed. Rep. of Germany

[21] Appl. No.: 111,399

[22] Filed: Jan. 11, 1980

Related U.S. Application Data

[63] Continuation of Ser. No. 861,277, Dec. 16, 1977, abandoned.

[30] Foreign Application Priority Data

Dec. 23, 1976 [DE] Fed. Rep. of Germany ....... 2658533

[51] Int. Cl.³ .............................................. A61B 6/00
[52] U.S. Cl. ...................................... 378/25; 378/22; 378/92; 378/99
[58] Field of Search ................... 250/445 T, 401, 407, 250/360

[56] References Cited

U.S. PATENT DOCUMENTS

| | | | |
|---|---|---|---|
| 2,667,585 | 1/1954 | Gradstein | 250/397 |
| 2,905,841 | 1/1957 | Meyer et al. | 313/55 |
| 3,250,916 | 5/1966 | Rogers | 250/314 |
| 3,389,253 | 6/1968 | Kok | 250/402 |
| 3,952,201 | 4/1976 | Hounsfield | 250/455 T |
| 4,057,725 | 11/1977 | Wagner | 250/445 T |
| 4,078,177 | 3/1978 | Tiemens | 250/445 T |
| 4,145,614 | 3/1979 | Kowalski | 250/445 T |

Primary Examiner—Alfred E. Smith
Assistant Examiner—T. N. Grigsby
Attorney, Agent, or Firm—Hill, Van Santen, Steadman, Chiara & Simpson

[57] ABSTRACT

In illustrated laminographic embodiments, longitudinal body layers are scanned by arranging individual x-ray tubes along a path or surface parallel to the body layer. The intensity of each conical beam focused on the body layer may be individually selected according to the absorption of the associated beam path through the body, for the sake of a fluoroscopic image of uniform brightness. For scanning either longitudinal or transverse body layers, a stationary detector may be utilized, sequentially activated conical or thin fan-shaped beams impinging on respective sets of time-shared detector locations to provide sets of measured values identified with the respective beams.

13 Claims, 5 Drawing Figures

APPARATUS FOR DISPLAYING FLUOROSCOPIC TOMOGRAPHIC IMAGES OF THE BODY

This is a continuation of application Ser. No. 861,277, filed Dec. 16, 1977 and now abandoned.

BACKGROUND OF THE INVENTION

A commonly assigned prior patent application Ser. No. 837,198 filed Sept. 28, 1977, (now abandoned in favor of application Ser. No. 058,869 filed July 19, 1979, also commonly owned), and corresponding to German Application P 26 47 167.0 filed Oct. 19, 1976, illustrates arrangements similar to the first and second figures herein. Methods are known, for example, from the "Encyclopedia of Medical Radiology", Vol. 1, Part 2, 1965, Pages 203 to 212 wherein tomograms are produced with x-rays or similarly penetrating radiation by scanning of the subject under examination with a beam of rays emanating from a source and wherein the beam which issues from the subject under examination acts upon a recording device, the source and recording device being moved in unison to bring about the scanning of the desired bodily layer.

As is known, in order to produce tomograms with x-rays, at least two parts of the required recording arrangement, i.e., radiation source, examination subject, and recording device, are moved relative to one another. Depending upon the methods and recording elements employed, the patient is, in most instances, kept motionless in medical diagnosis, so that a movement of the x-ray tube and the photographic cassette takes place. However, this necessitates the acceleration and deceleration of relatively large masses, which is expensive because it is desirable to accomplish this in as short a period of time as possible during a radiographic procedure.

However, with respect to the conventional tomographic procedure, the decisive factor is the process of initiating relative motion, because this determines the time requirement, particularly in the case of only a one sided-operating cycle. In the case of conventional apparatus for displayng linear layers, the shortest photographic times have proved to be of the order of 600 milliseconds. More rapid recording cycles are only possible at considerable expense.

However, in so doing, only a reduction by half of the shortest tomographic times which are otherwise possible can be achieved as a rule. In order to photograph moving organs, such as the heart, tomographic times of 80 msec would have to be obtained. Taking into consideration the movement sequences of individual parts of the heart within the heart phase, moreover, a tomographic time of 20 msec appears desirable. Rapid movements such as this cannot be obtained with the mechanical means presently available.

SUMMARY OF THE INVENTION

The object which is the basis of the invention consists in disclosing a method and an assembly for the production of tomograms with x-rays or similarly penetrating radiation, with which tomographic times below 80 msec, and preferably at least down to 20 msec can be obtained, the assembly having a simple construction as compared with the solution provided by the prior patent application.

By utilizing a plurality of radiation sources which are arranged in rows (or in surface arrays), and which can be switched on in a random sequence, the operating cycle time of the tomogram can be shortened. This is based particularly on the fact that the radiation sources; i.e., the x-ray tubes shielded such that they confine radiation to the desired path, need not be set in motion. In the case of a rapid tomogram, it is sufficient to move the lightest element; i.e., the recording element, such as a film cassette. In an arrangement such as this, with an x-ray beam being shifted from focal spot to focal spot, the demand for a short photographic period can also be realized, for example, if, given a path of movement of approximately one meter (1 m), a relatively large number of focal spots, for example twenty, are arranged in succession, these focal spots measuring approximately 0.3×0.3 to 3×3 mm, particularly 1×1 mm in size, (corresponding to the focal spots normally encountered in x-ray diagnosis). Switching on of the radiation sources can proceed in a known fashion by virtue of the fact that the cathodes, which are ready for operation, are blocked by a grid whose blocking potential is interrupted during the period for which the individual radiation sources are to be switched on. The interruption can be triggered by the moving recording element as a function of its movement by arranging switches such as magnetic switches, mechanical switches, etc., along its path of movement which switches can be successively actuated by the element. However, an electronic triggering, for example, using light barriers, magnetic switches, etc., is also possible in the desired sequence. This is of particular importance during recording of the image with radiation-measuring probes and storage in a data store, such as in the case for example of computer tomography (compare e.g. U.S. Pat. No. 3,778,614). In that case the radiation sources can be switched on and the data stores controlled from a central control unit.

In one embodiment according to the present invention, a straight arrangement of approximately twelve tubes may have a length of sixty centimeters, for example, for photographing planar layers, so that the tubes are disposed at intervals of 5.0 cm. Although a different type of circuit switching is also possible, tubes are expediently employed which contain a switching grid. An individual grid is then associated with each cathode, with which grid issuance of the electrons can be blocked. In an operating cycle all the cathodes can thus readily be sequentially activated in twenty milliseconds or even faster. It is only necessary for switching elements to be actuated in synchronism with the recording arrangement, such as the movement of a film cassette along its path of displacement or in accordance with the input into a data store. A limit on the speed is given in the case of photographs only by the requirements of acceleration of the cassette and the sensitivity of the photographic material. The switching process can proceed at a random speed. In utilizing a conventional cassette and a known x-ray film, a duration of photographic exposure of only twenty milliseconds should be obtainable. Electronic image storage, in utilizing a detector system as the recording device, such as in the case of computer tomography, is free of this restriction, because moved masses are here entirely avoided.

By utilizing a plurality of x-ray tubes, it is no longer necessary to adhere so strictly to a construction which can be accommodated in a vacuum tube. X-ray tubes may be constructed per se in a random manner and in a random arrangement. Thus, in addition to the arrangement in a straight line which is necessary for conventional tomograms, an arrangement in surface arrays, or in a plurality of planes, respectively, is also possible. This provides the additional possibility of utilizing randomly winding paths, such as curved paths, or meandering paths, during scanning. By surface-scanning, it is possible to obtain very thin layers with a high degree of blurring outside this layer. The utilization of a plurality of x-ray tubes which are arranged in a surface array offers the possibility of varying the intensity of the produced rays over the surface distribution; for example, in the manner of a harmonization of the resulting fluoroscopic image through the production of less intensity at those locations where little absorption prevails than at those locations where a great deal of absorption is expected, corresponding to thin and thick locations of the body to be examined.

For computer tomography as is known, for example, from U.S. Pat. No. 3,778,614, instead of a radiation source which is moved along a circular path, it is possible to arrange a plurality of tubes on a circular support mounting and to successively switch them on such that the radiation emission corresponds to that which could be obtained with an x-ray tube moved in a circular path. The rotation of a single tube can be satisfactorily simulated with a large number of individual tubes.

Regarding tubes arranged for the production of transverse layer images, use can be made of a construction corresponding to that of U.S. Ser. No. 779,671 filed Mar. 21, 1977. The additional advantage resulting here is that, in addition to the shortening of the path of rotation, the effect is achieved that a number of different stationary sets of detectors corresponding to the number of sources (e.g. five) are simultaneously active to supply measured values without any need for coupling to the data store via moving conductors. As the sources are shifted, different sets of the stationary circular array of detectors respond thereto, so that the same detectors serve a plurality of sources.

Other objects, features and advantages of the invention will be apparent from the following detailed description taken in connection with the accompanying drawings.

DETAILED DESCRIPTION

Figure 1:
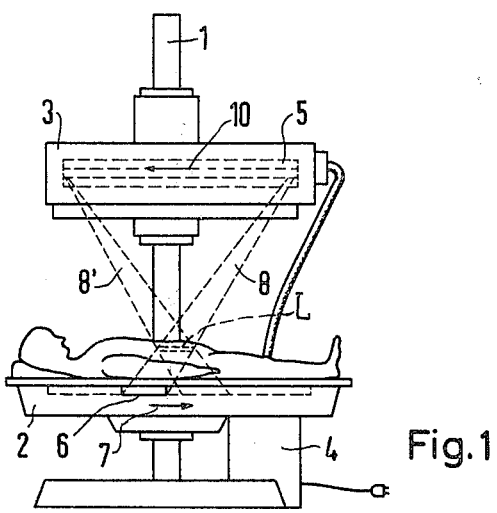
FIG. 1 illustrates a diagrammatic elevational view of a tomographic x-ray apparatus constructed in accordance with the invention.

FIG. 1 illustrates an x-ray apparatus in which a patient support 2 and a radiation source 3 are mounted on a support column 1 in a vertically displaceable fashion. In addition, an electric supply system 4 is provided for the purpose of operation, which is to be supplied with current from the mains. For producing a photographic exposure according to the invention, an x-ray tube 5 is set in operation by means of the current supply system 4, on the one hand, and an x-ray film cassette 6 housed in table 2 is set in motion in the direction of an arrow 7 also by means of said current supply installation. A focal spot of approximately $2 \times 2$ mm$^2$ is thereby produced in the tube, which leads to the production of a cone of rays 8 and which is moved in the direction of arrow 10 in a direction opposite that of the cassette through shifting of the switching-on of cathodes referenced with 9, FIG. 2.

Figure 2:
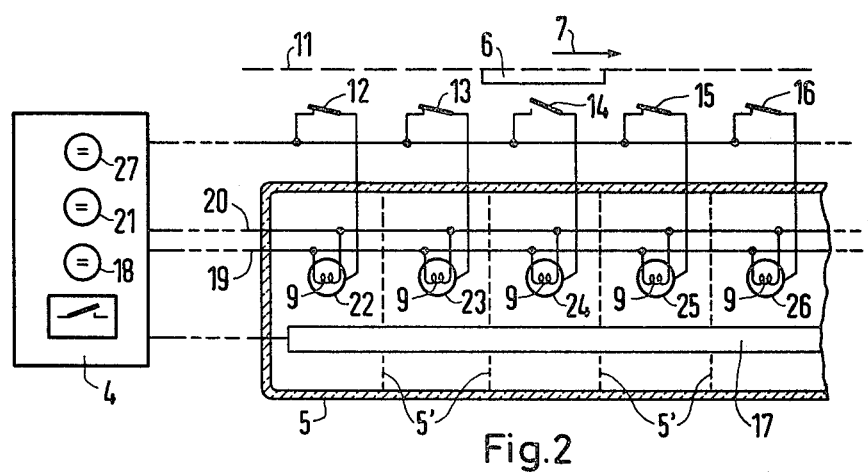
FIG. 2 is a basic circuit diagram showing a series of focal spots which can be successively actuated.

Switching on of the cathode 9 is synchronized in a simple fashion with the movement of cassette 6 by associating adjacently disposed switches 12 through 16 with the path of movement 11 indicated in FIG. 2 by a dash line. All these switches are closed and are briefly opened only when cassette 6 slides by. One cathode 9 is thereby actuated in each instance, so that a focal spot is obtained on anode 17 traveling in the direction of arrow 7 (for the diagrammatic showing of FIG. 2) in steps of 2.5 cm. (The physical arrangement of grids such as 22-26 in the apparatus of FIG. 1 would be in the direction of arrow 10, so that opening of switch 12 would produce beam 8, and opening of the final switch of the series would produce beam 8'.)

Actuation of the focal spots proceeds in a simple fashion by applying a DC voltage 18 from current supply installation 4 in order to produce x-rays between cathode 9 and anode 17, on the one hand. A DC voltage 21 is connected between conductors 19 and 20, on the other hand, said DC voltage bringing cathode 9 to a state of incandescence. In addition, there is connected between cathode 9 and its associated grids 22 through 26, an additional DC voltage 27 which is sufficient to prevent issuance of electrons from 9 onto anode 17. Only by disconnecting the blocking voltage through opening one of the switches 12 through 16 can electrons be emitted and x-rays be produced on anode 17. Thus, as indicated on FIG. 1, an x-ray beam 8 is produced which travels in the direction of arrow 10 to position 8'. A fluoroscopy of movement; i.e., the customary conditions for the tomogram, is thereby achieved.

Figure 3:
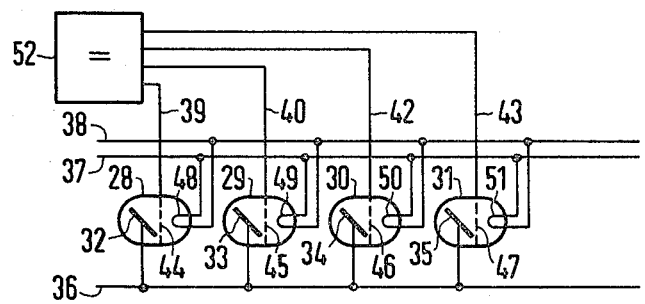
FIG. 3 illustrates an arrangement of a plurality of x-ray tubes in a row capable of successive actuation.

FIG. 3 illustrates an arrangement wherein the radiation sources consisting of cathodes 9 and blocking grids 22 through 26 are separated from one another at the separation lines 5' indicated by broken lines in FIG. 2. In this manner, a construction is obtained in which x-ray tubes 28 through 31 are assembled in a row in spatial intervals of 5 cm from one another. Anode 17 is here divided into separated anodes 32 through 35. The vacuum-tight lateral walls of tubes 28 through 31 have been positioned on lines 5' of FIG. 2. Operation proceeds in the same manner as in the case of the arrangement according to FIG. 2 by virtue of the fact that the anode voltages are connected via lines 36 and 37, and the cathode heating voltage is connected via lines 37 and 38. The grid voltages are connected to grids 44 through 47 via lines 39 through 43. In this fashion, as in accordance with FIG. 2, a synchronized transmission of electrons from cathodes 48 through 51 to anodes 32 through 35 is controllable by means of switches such as shown at 12-16 in FIG. 2. Accordingly, the result illustrated in FIGS. 1 and 2 is achieved with separated tubes.

Figure 4:
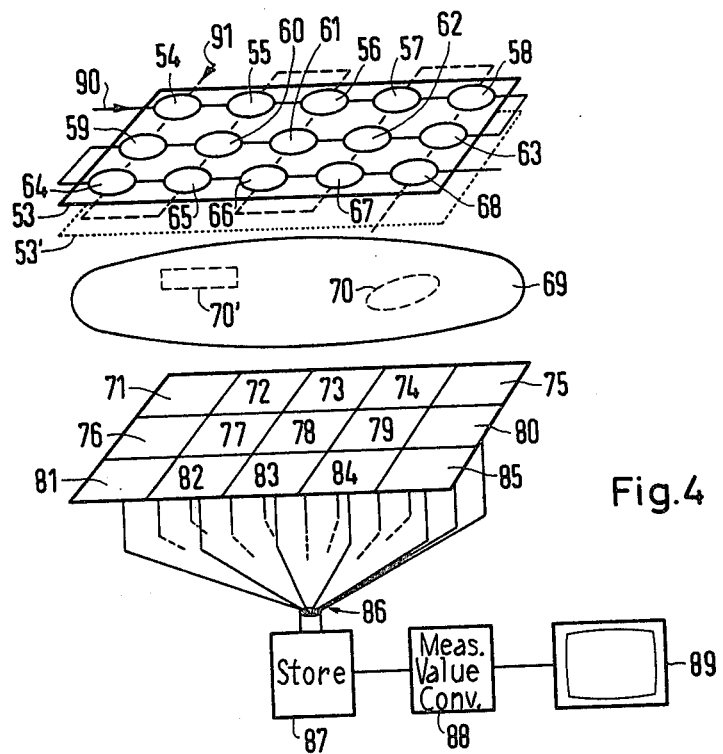
FIG. 4 illustrates a surface array of a plurality of x-ray tubes disposed opposite a detector construction of a like arrangement, and wherein the arrangement of tubes in an additional plane is furthermore indicated.

In FIG. 4, an arrangement is illustrated wherein there are disposed, in a plane 53, tubes 54 through 68 in three rows, each with five tubes; i.e., 54 through 58, 59 through 63, and 64 through 68. Basically, this arrangement corresponds to that according to FIG. 2 and 3. In the case of this arrangement, also, the control of the focal spot actuation is possible by means of mechanical or electric stepping switches. Operation proceeds as in the case of FIGS. 2 and 3.

Assembly 53 can be supplemented by an additional plane 53' indicated by a dotted line. In this plane, also, it is possible to accommodate tubes in a plurality of rows corresponding to tubes 54 through 68. Through such an addition, in which the tubes are positioned in relation to those of array 53 such as to fill gaps, it is possible to obtain spatially arranged measured values which can later be analyzed in any desired manner. The effect of the tubes housed in 53', in the displaced position relative to 53, already affords the possibility of obtaining an additional tomogram without having to make adjustments on the apparatus. Further x-ray tubes accommodated in additional planes could increase the effect even further.

Assembly 53 is applicable, for example, in order to determine the precise shape and position of foreign bodies 70, 70' in a body 69. In relation to assembly 53, there is disposed behind body 69 a recording panel consisting of detectors 71 through 85. The latter may be photo multipliers which are preceded by crystals consisting of a fluorescent material, such as e.g. cesium iodide which is activated with thallium, in order to improve the effect of the x-radiation. Detectors 71 through 85 are connected to a store 87 via lines 86 of which only a few are fully indicated in the drawing for the purpose of a clear overview. In addition to the signals produced in detectors 71 through 85 by means of tubes 54 through 68, signals can also be picked up which are produced with tubes from the plane 53' and from additional nonillustrated planes, and these signals can be stored in readiness for further processing. A measured value converter 88 is connected to store 87 and a television display unit 89 is connected to the measured value converter.

Figure 5:
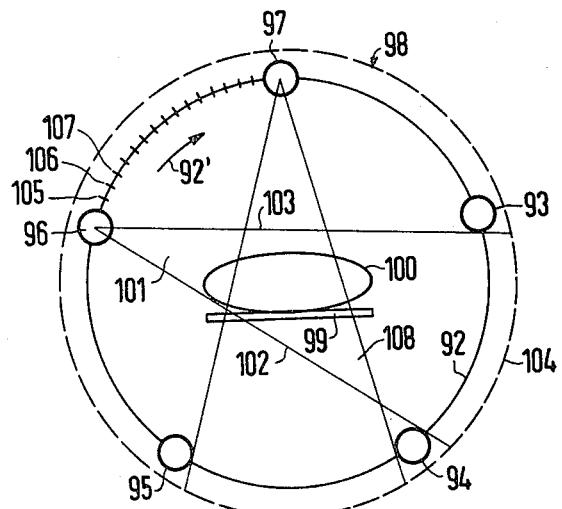
FIG. 5 shows the arrangement of a plurality of tubes on a circular frame.

By virtue of the recording of tomographic images with the stationary panel consisting of detectors 71 through 85; i.e., without a mechanically moved part (cassette), the scanning operation is effected with electronic sequence switching which simulates an operating cycle such as indicated in FIG. 2. The switching elements additionally described in refernce to FIG. 5 are, for example, useful to this end. The scanning path can be meander-like, and can be realized through actuation of tubes 54 through 68 in the time sequence represented by the direction of arrow 90; i.e., through the operating cycle of the actuation (or switching on) of the tubes from 54 to 58, then from 63 to 59, and from 64 through 68. A scanning is likewise possible in the time sequence represented by the direction of arrow 91 along the dash line running transversely to the aforementioned path following the solid line connected with arrow 90; i.e., from tube 54 to 64, back from 65 toward 55, then from 56 toward 66, back from 67 toward 57, and finally, from 58 toward 68. Upon completion of the operating cycle of actuation of x-ray tubes 54 through 68, additional signals stored in data store 87 can be called up into measured value converter 88 for constructing an x-ray image from these signals, which can be output on display unit 89 in the form of a viewable image.

FIG. 5 indicates the application of the invention in computer tomography. Five x-ray tubes 93 through 97 are here mounted in equal spatial intervals from one another on a rotating frame 92 which represents a ring-shaped frame. In addition, frame 92, as indicated by arrow 92' is rotatably mounted in a manner not illustrated.

Frame 92 comprising tubes 93 through 97 is surrounded by a detector 98 which is formed from a plurality of individual measuring probes. In the center of this rotating frame 92, there is disposed a support table 99 on which a patient 100 can be positioned during examination. The method of operation of the assembly is explained in the following on the basis of tube 96, by way of example.

At the commencement of the examination of patient 100, this tube 96 is activated such that a fan-like beam 101 is produced which penetrates patient 100 and strikes the section 104 disposed between marginal rays 102 and 103 of ring shaped detector 98 such that measured values are obtained therefrom. With a further movement in the direction of arrow 92', further actuations can take place at points 105, 106, and 107, indicated by dashes, and, as indicated further, up to the initial position of tube 97, such that an effect can be achieved which, in the case of a stationary assembly, would necessitate the mounting of tubes at all points 105, 106, 107, etc. However, while the tube 96 is being moved to the original position of tube 97, all the remaining tubes 97 and 93 through 95 are also advanced, so that altogether the whole circle has been scanned. There is associated with all tubes a fan-shaped beam such as that associated with tube 96, which is referenced with 101, or such as that which, in the case of tube 97, is referenced with 108. In this manner, the entire circle is scanned with only a 1/5 of a revolution, i.e., with only 72° of (simultaneous) rotation of the sources 93–97. By analogy to the case of FIGS. 1, 2, etc., control can be mechanically synchronized here with the movement of sources 93-97 during the recording cycle.

In each of the embodiments where a stationary set of detectors is used, for example in embodiments such as FIG. 5 without a mechanical operating cycle of photographic parts (cassette, etc.), it would appear expedient to employ program switches, or angle indicators (e.g. coupled with frame 92, FIG. 5), etc., which are known per se. For example, in one embodiment, circularly arranged contacts may be employed with which a motor-driven wiper element or the like is associated to form of a switching signal generator. Through selection of the drive speed (or angular velocity) of the wiper or other rotary element and the positioning of the associated stationary contacts in the circle; i.e., the spatial intervals between the contacts uxed, all conceivable variations of the chronological and local sequence of actuation (or switching on) of the radiation sources can be obtained. In this way also, a connected store can be set in operation synchronously with the recording cycle. On the other hand, however, there are also other known switching measures and synchronizations, for example, from computer tomography, which can be used.

The reproduction of the recorded image can take place in the manner conventional in computer tomography in that the measured values collected in a store are supplied to a measured value converter which constructs, from the signals, a television x-ray image which can be reproduced on a display unit.

In all assemblies, x-ray tubes can be used whose focal spot size is approximately 2×2 mm with an operating voltage of 70 kV to 150 kV, particularly 100 kV. As the blocking potential, a voltage of approximately 1 to 3 kV is sufficient, which is connected between the cathode and the grid. It is only this grid-cathode voltage which needs to be switched in order to permit the scanning or pulsing of one or more beams to proceed in the manner desired.

It will be apparent that many modifications and variations may be effected without departing from the scope of the novel concepts and teachings of the present invention.

SUPPLEMENTARY DISCUSSION

In each of the embodiments of FIGS. 1–4, the radiation sources are arranged along a path disposed for scanning of a longitudinal body layer by sequential activation thereof. The conical beams from the successive sources in FIG. 1 are each focussed on a longitudinal layer such as indicated at L in FIG. 1 which extends longitudinally of the patient, and which may exhibit a horizontal planar disposition (where column 1 is vertical). The operation of the apparatus of FIG. 1 in scanning a longitudinal body layer such as L may be simulated with the apparatus of FIGS. 3 and 4, in which case each of the sources comprises a separate x-ray tube for providing a conical beam similar to that shown at 8 and 8' in FIG. 1. Thus each of the sources such as 28–31 in FIG. 3 and such as 54–68 in FIG. 4 is essentially delimited to focus on a common layer such as indicated at L in FIG. 1. As each source is activated, a reading may be taken from the set of detectors from a total group such as 71–85, FIG. 4, which set senses the transmitted energy with respect to the longitudinal body layer (such as L, FIG. 1) which is being examined. In this case, the detectors would cover the area traversed by the film of cassette 6, FIG. 1, and the number of sources and detectors would be such as to give the desired resolution in the displayed image of the layer. For sources arranged as in FIG. 3 or FIG. 4 with conical beams, the layer L being irradiated for examination would have a somewhat oval or oblong shape. The detector array would conform to the transmitted radiation from layer L in the plane of the path of cassette 6, and may of course have a rectilinear outline falling within the transmitted radiation pattern.

The sources 93–97 in FIG. 5 provide fan-shaped beams with a thickness (the dimension at right angles to the plane of FIG. 5) which is very small so as to irradiate only a thin cross sectional layer of body 10. The number of stationary detector elements at 98 is selected in accordance with the desired resolution in the image to be generated. The set of detectors such as 104 associated with each source shifts with each increment of movement of the source, and accordingly the memory for storing the measured values may have five memory segments each corresponding to one of the sources 93–97 for simultaneously converting and storing measured values, each segment providing predetermined storage locations for each of the angular positions of the associated source. The end result is then a stored set of measured values identified with each predetermined angular position of an incident fan-shaped beam, with the stored sets representing successive equal angular displacements over a total angle of 360°.

In each embodiment with a stationary array or stationary arrays of separate x-ray sources, separate individual values of anode voltage may be provided between each cathode and the associated anode so as to adapt each conical beam to its respective path length within the body, for example, so that the intensity of the beam is greater in the case of slanting paths as at 8 and 8' in FIG. 1, while the beams more nearly normal to layer L have progressively less intensity.

With respect to a transverse layer as in FIG. 5, the sources may be arranged so that each covers a range of positions with a relatively constant path length within the body such as 100, each source then having a constant anode potential adapted to its respective associated path length. Alternatively the anode potential may be changed for each source position in accordance with the average path length encountered in such position.

In view of the foregoing it will be apparent that the teachings of the present invention may be adapted to simulate various types of known tomographic apparatus, with the advantage of simulating movement of a single x-ray source through locii lying on curved or circular, single or multiple strip, or curved or circular, single or multiple surface configurations by the provision of corresponding series or arrays of separate individually adjustable x-ray tubes, with anode voltages adapted to the respective path lengths within the body. In each case grid blocking potential may be removed from plural tubes simultaneously if feasible, and the tube may be moved over limited distances with the detector array stationary, and with individual detectors serving different sources in successive simultaneous actuations of the same sources, with individual tubes as shown in FIG. 3, arranged in a row as indicated at 5 in FIG. 1, for example, it is possible to manage with fewer tubes providing the tubes are additionally moved. However, the movement only has to overcome the interval between the initial tube locations and may take place more slowly than if the entire length of the layer had to be covered in a given time. By sequentially switching on the tubes in each successive position to which the series is moved, the same result is achieved as with movement of a single tube. Thus instead of pulsing a single tube twelve times (e.g. at intervals of 5.0 cm) along path 10, FIG. 1, the same result is achieved by pulsing six tubes spaced ten centimeters apart, in sequence in the direction of arrow 10, during movement of cassette 6 in the direction of arrow 7, and then shifting the tubes in the direction of arrow 10 by 5.0 cm, and pulsing the tubes in a reverse sequence as the cassette 6 returns toward its initial position (moving in a direction opposite to arrow 7, FIG. 1). Of course, the same result could be obtained with the use of a suitable array of stationary or shiftable detectors disposed over the path of travel of cassette 6.

We claim as our invention:

1. An apparatus for obtaining body layer images with x-ray or similarly penetrating rays, said apparatus comprising radiation source means and a recording unit operable to produce a scanning operation in which a beam coming from the source means penetrates the subject to be examined and the beam emerging from the body is caused to act on the recording unit, the source means comprising a row of x-ray tubes lying in a common plane and each being switched on for a time period required to operate the recording unit, the x-ray tubes being separated from one another and being disposed for scanning a longitudinal body layer parallel to said common plane by sequential activation thereof, the cathode of each tube having a switching grid for controlling emission therefrom, and means for sequentially actuating said grids in synchronism with a shifting of the recording unit to effect emission of an x-ray beam from the x-ray tubes in said row in such a sequence that the longitudinal body layer parallel to the plane of said sources is scanned while all other layers are blurred.

2. An apparatus according to claim 1, with said row of x-ray tubes defining a straight line path in the plane of said sources, and electrical lines connected in parallel with said row of x-ray tubes for supplying anode voltage to each of said tubes.

3. An apparatus as claimed in claim 1, characterized in that the x-ray tubes are arranged in a surface array parallel to the longitudinal body layer to be examined.

4. An apparatus as claimed in claim 1, characterized in that the x-ray tubes are additionally moved during the recording.

5. An apparatus as claimed in claim 1, characterized in that the x-ray tubes each transmit a conical beam to the recording unit.

6. An apparatus as claimed in claim 1, characterized in that the x-ray tubes are arranged in at least one row and each transmits a conical beam to the recording unit.

7. An apparatus as claimed in claim 1, with the intensity of the beams from the respective tube during a scanning operation being respectively selected in dependence upon the body thickness to be penetrated by the beams in such a way that their intensity is higher where the beams have to penetrate through thick areas and lower where they have to penetrate through thin areas of the body under examination.

8. An apparatus for obtaining body layer images with x-ray or similarly penetrating rays, said apparatus comprising a source and recording unit operable to produce a scanning operation in which a beam coming from the source penetrate the subject to be examined and the beam emerging from the body is caused to act on the recording unit, the source comprising a plurality of radiation sources which are arranged along a path and each of the radiation sources being switched on for a time period required to operate the recording unit, the radiation sources being formed by x-ray tubes separated from one another and disposed for scanning a longitudinal body layer by sequential activation thereof, the x-ray tubes being arranged in a surface array parallel to the longitudinal body layer to be examined, and the x-ray tubes being additionally moved during the recording.

9. An apparatus for obtaining body layer images with x-ray or similarly penetrating rays, said apparatus comprising radiation source means and recording means for effecting a coordinated scanning operation in which a beam coming from the source means penetrates the subject to be examined and the beam emerging from the body is caused to act on the recording means, the source means comprising a row of x-ray tubes lying in a common plane and each being switched on for a time period required to activate the recording means, the x-ray tubes being separated from one another and being disposed for scanning a longitudinal body layer parallel to said common plane by sequential activation thereof in conjunction with a coordinated scanning operation of the recording means, the cathode of each tube having a switching grid for controlling emission therefrom, and means for sequentially actuating said grids in coordination with a scanning operation of the recording means to effect emission of an x-ray beam from the x-ray tubes in said row in such a sequence that the longitudinal body layer parallel to the plane of said sources is effectively scanned by said recording means while all other layers are blurred, characterized in that the x-ray tubes are additionally moved during the recording.

10. An apparatus for obtaining body layer images with x-ray or similarly penetrating rays, said apparatus comprising radiation source means and recording means for effecting a coordinated scanning operation in which a beam coming from the source means penetrates the subject to be examined and the beam emerging from the body is caused to act on the recording means, the source means comprising a row of x-ray tubes lying in a common plane and each being switched on for a time period required to activate the recording means, the x-ray tubes being separated from one another and being disposed for scanning a longitudinal body layer parallel to said common plane by sequential activation thereof in conjunction with a coordinated scanning operation of the recording means, the cathode of each tube having a switching grid for controlling emission therefrom, and means for sequentially actuating said grids in coordination with a scanning operation of the recording means to effect emission of an x-ray beam from the x-ray tubes in said row in such a sequence that the longitudinal body layer parallel to the plane of said sources is effectively scanned by said recording means while all other layers are blurred, characterized in that the x-ray tubes each transmit a conical beam to a respective different region of the recording means.

11. An apparatus for obtaining body layer images with x-ray or similarly penetrating rays, said apparatus comprising radiation source means and recording means for effecting a coordinated scanning operation in which a beam coming from the source means penetrates the subject to be examined and the beam emerging from the body is caused to act on the recording means, the source means comprising a row of x-ray tubes lying in a common plane and each being switched on for a time period required to activate the recording means, the x-ray tubes being separated from one another and being disposed for scanning a longitudinal body layer parallel to said common plane by sequential activation thereof in conjunction with a coordinated scanning operation of the recording means, the cathode of each tube having a switching grid for controlling emission therefrom, and means for sequentially actuating said grids in coordination with a scanning operation of the recording means to effect emission of an x-ray beam from the x-ray tubes in said row in such a sequence that the longitudinal body layer parallel to the plane of said sources is effectively scanned by said recording means while all other layers are blurred, the intensity of the beams from the respective tubes during a scanning operating being respectively selected in dependence upon the body thickness to be penetrated by the beams in such a way that their intensity is higher where the beams have to penetrate through thick areas and lower where they have to penetrate through thin areas of the body under examination.

12. An apparatus for obtaining body layer images with x-ray or similarly penetrating rays, said apparatus comprising radiation source means and recording means for effecting a coordinated scanning operation in which a beam coming from the source means penetrates the subject to be examined and the beam emerging from the body is caused to act on the recording means, the source means comprising a row of x-ray tubes lying in a common plane and each being switched on for a time period required to activate the recording means, the x-ray tubes being separated from one another and being disposed for scanning a longitudinal body layer parallel to said common plane by sequential activation thereof in conjunction with a coordinated scanning operation of the recording means, the cathode of each tube having a switching grid for controlling emission therefrom, and means for sequentially actuating said grids in coordination with a scanning operation of the recording means to effect emission of an x-ray beam from the x-ray tubes in said row in such a sequence that the longitudinal body layer parallel to the plane of said sources is effectively scanned by said recording means while all other layers are blurred, characterized in that the x-ray tubes are arranged in a surface array along a line parallel to the longitudinal axis of the body.

13. An apparatus according to claim 12 with said surface array having a plurality of rows of x-ray tubes, the x-ray tubes of each row being arranged along a line parallel to the longitudinal axis of the body.

* * * * *